(12) United States Patent
Dippl et al.

(10) Patent No.: US 11,445,991 B2
(45) Date of Patent: Sep. 20, 2022

(54) X-RAY DEVICE AND METHOD FOR MEDICAL IMAGING

(71) Applicant: SIEMENS HEALTHCARE GMBH, Erlangen (DE)

(72) Inventors: Thomas Dippl, Pressath (DE); Thomas Schmitt, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 95 days.

(21) Appl. No.: 16/079,673

(22) PCT Filed: Dec. 14, 2016

(86) PCT No.: PCT/EP2016/080923
§ 371 (c)(1),
(2) Date: Aug. 24, 2018

(87) PCT Pub. No.: WO2017/144138
PCT Pub. Date: Aug. 31, 2017

(65) Prior Publication Data
US 2019/0046138 A1  Feb. 14, 2019

(30) Foreign Application Priority Data
Feb. 24, 2016  (DE) ..................... 10 2016 202 847.2

(51) Int. Cl.
*A61B 6/00* (2006.01)
*A61B 6/04* (2006.01)
*A61B 6/03* (2006.01)

(52) U.S. Cl.
CPC .......... *A61B 6/4452* (2013.01); *A61B 6/0407* (2013.01); *A61B 6/4429* (2013.01); *A61B 6/4464* (2013.01); *A61B 6/547* (2013.01); *A61B 6/587* (2013.01); *A61B 6/032* (2013.01); *A61B 6/0421* (2013.01)

(58) Field of Classification Search
CPC ... A61B 6/4452; A61B 6/0407; A61B 6/4429; A61B 6/4464; A61B 6/547; A61B 6/587; A61B 6/032; A61B 6/0421
See application file for complete search history.

(56) References Cited

U.S. PATENT DOCUMENTS 6,282,264 B1    8/2001  Smith et al.
9,125,570 B2 *  9/2015  Pelc ................. A61B 6/025
(Continued)

FOREIGN PATENT DOCUMENTS

CN    202288318 U    7/2012
CN    103654813 A    3/2014
(Continued)

*Primary Examiner* — David P Porta
*Assistant Examiner* — Mamadou Faye
(74) *Attorney, Agent, or Firm* — Laurence A. Greenberg; Werner H. Stemer; Ralph E. Locher

(57) ABSTRACT

An X-ray device for carrying out X-ray scans is configured for a simplified procedure. The X-ray device has an image receptor which operates in conjunction with an X-ray generator to carry out X-ray scans of a patient, and a patient table. A tabletop of the patient table which is used to position the patient during the X-ray scans, is immovable in the table plane. Instead, the image receptor is disposed in a longitudinally and transversely movable manner relative to the tabletop parallel to the table plane.

8 Claims, 2 Drawing Sheets

(56) References Cited

U.S. PATENT DOCUMENTS

| | | |
|---|---|---|
| 2002/0080921 A1 | 6/2002 | Smith et al. |
| 2003/0091151 A1 | 5/2003 | Horbaschek et al. |
| 2004/0264626 A1* | 12/2004 | Besson ................. A61B 6/563 378/4 |
| 2007/0183587 A1* | 8/2007 | Baumann ............. A61B 6/4452 378/196 |
| 2008/0285723 A1 | 11/2008 | Lumma et al. |
| 2012/0045105 A1 | 2/2012 | Engel et al. |
| 2014/0072101 A1* | 3/2014 | Park ....................... A61B 6/462 378/62 |
| 2015/0265231 A1* | 9/2015 | Stopp ....................... A61N 5/01 378/62 |
| 2016/0073985 A1* | 3/2016 | Moon ................. A61B 6/0457 378/181 |

FOREIGN PATENT DOCUMENTS

| | | |
|---|---|---|
| CN | 203662770 U | 6/2014 |
| DE | 2519153 A1 | 11/1976 |
| DE | 102010034918 A1 | 2/2012 |
| DE | 202015106190 U1 | 2/2016 |
| EP | 2609859 A1 | 7/2013 |
| WO | 2014171647 A1 | 10/2014 |

* cited by examiner

X-RAY DEVICE AND METHOD FOR MEDICAL IMAGING

BACKGROUND OF THE INVENTION

Field of the Invention

The invention relates to an X-ray device for a medical imaging system, particularly for radiological examination of patients. The invention also relates to a method for medical imaging, wherein the method can be carried out in particular using the X-ray device according to the invention.

To carry out an X-ray scan of a patient, either a Bucky wall stand, i.e. a vertical patient table, is used, particularly for examinations of the thorax, or else the patient lies on a horizontal floating-top table. In the case of such a patient table, the image receptor (X-ray detector or cassette) is usually mounted in a detector cabinet under the patient table.

To carry out an X-ray scan, the X-ray generator, patient and image receptor must be suitably positioned relative to one another. For this purpose, the known patient tables having a so-called floating tabletop are used. This means that the tabletop can be moved both in both the longitudinal direction of the table (lengthwise) and in the transverse direction of the table (crosswise) in order to be able to X-ray a patient from head to foot without repositioning. For this purpose, the detector cabinet housing the image receptor can also be displaced in the longitudinal direction of the table.

The procedure for performing X-ray scans is comparatively complex. Particularly time-consuming here is the correct positioning of the patient relative to the X-ray generator and image receptor.

DE 25 19 153 A2, U.S. 2002/0080921 A1 and DE 10 2010 034 819 A1 disclose X-ray devices in which the X-ray generator and image receptor are moved relative to the patient table independently of the patient table using a stand or a C-arm.

SUMMARY OF THE INVENTION

An object of the present invention is to simplify the procedure for carrying out X-ray scans. This object is achieved by an X-ray device as, a method as claimed and by a computer program as claimed. Advantageous embodiments of the invention are set forth in the sub claims dependent claims.

The advantages and embodiments explained below in connection with the X-ray device also apply analogously to the inventive method and the inventive computer program and vice versa.

The basic concept of the present invention is to dispense completely with longitudinal or transverse movement of the patient table, or more specifically of the tabletop of the patient table. Instead, the image receptor shall be movable in the longitudinal and transverse direction with the tabletop remaining stationary. In other words, it is proposed to use a floating detector cabinet instead of a floating tabletop.

Instead of time-consuming, active positioning of three system components (X-ray generator, patient table, image receptor) relative to one another, according to the invention only two components need to be positioned, namely the X-ray generator and image receptor. In other words, only the X-ray generator and image receptor are moved, with the tabletop remaining stationary.

Because of the fixed tabletop, the position and posture of the patient remains unchanged throughout the radiographic procedure. The patient does not need to be displaced during the examination. It is also unnecessary for the patient to be moved on the tabletop (repositioning). At the same time, the complex drive and control means for moving the heavy tabletop are eliminated. The patient table comprises fewer components, can be manufactured more easily and inexpensively, thereby reducing the costs for the X-ray device as a whole. It is only necessary to provide additional drive and control means for the significantly smaller and lighter detector cabinet if the image receptor actually has to be moved using an electric motor drive. In a particularly simple and cost-effective embodiment of the invention, the image receptor is moved manually without motor drive.

If the longitudinal and transverse movement of the detector cabinet is executed in a motorized manner, it is advantageously provided that the image receptor is positioned automatically. Said image receptor is preferably moved in accordance with a movement of the X-ray generator and/or according to a position of X-ray generator (attained due to such a movement). In particular, this movement is designed such that the image receptor tracks the X-ray generator. In other words, the movement of the image receptor is linked to the movement of the X-ray generator.

This linkage can be implemented both via a motorized control and via a mechanical linkage. In other words, in a particular cost-effective solution, the image receptor can be linked to the X-ray generator in a purely mechanical manner, particularly such that the image receptor always tracks the movement of the X-ray generator on a 1:1 basis. Alternatively, drive-controlled, preferably automatic positioning of the image receptor is possible which is implemented using suitable control of corresponding motorized drives. In this case no mechanical connection between the X-ray generator and the image receptor is required. Instead, motorized drives are provided for all the axes. In a preferred embodiment of the invention, the corresponding motor control is linked to suitable means for detecting the position of the X-ray generator or image receptor so that the drive motors can be controlled according to the positions detected.

In another embodiment of the invention it is provided to rotate the image receptor in the table plane, or more precisely to dispose it so as to rotate about an axis of rotation perpendicular to the table plane and/or to tilt the image receptor relative to the table plane, or more precisely to dispose it so as to tilt about a tilt axis parallel to the table plane. In this case the image receptor can assume any angular positions relative to tabletop. As a result, the orientation of the image receptor can be changed (manually or in a motorized manner), e.g. in order to fully utilize the diagonal of the image receptor in the case of a spinal column X-ray scan or in order to ensure that, in the case of oblique irradiation, the central X-ray beam is perpendicular to the image plane of the image receptor.

Such a rotation of the image receptor if preferably linked to a corresponding rotation of the beam limiting device (collimator) of the X-ray generator. In other words, the image receptor preferably not only moves in accordance with a (linear) movement of the X-ray generator in the table plane relative to the tabletop, i.e. in the longitudinal direction of the table and/or in the table transverse direction or in accordance with an attained scanning position of the X-ray generator, but a rotational movement also takes place in accordance with a rotational movement or an attained position of the collimator of the X-ray generator. For this purpose, in an embodiment of the invention, the collimator is designed to be able to rotate (manually or in a motorized manner, e.g. under remote control) about the central X-ray beam.

In this case, the image receptor therefore executes not only a tracking movement with respect to the movement of the X-ray generator in the table plane (xy-plane), but also a tracking movement with respect to part of the X-ray generator, namely with respect to the rotational movement of the collimator.

Tilting of the image receptor is preferably linked to a corresponding tilting movement of the X-ray generator. In other words, the image receptor preferably not only moves in accordance with a (linear) movement of the X-ray generator in the table plane relative to the tabletop, i.e. in the longitudinal direction of the table and/or in the table transverse direction or in accordance with an attained scanning position of the X-ray generator, but a tilting movement also takes place in accordance with a tilting movement of the X-ray generator with respect to the table plane (xy-plane) or an attained position of the X-ray generator.

Additionally, the linear and/or rotational or tilting movement of the image receptor can also take place in a manner dependent on the patient organ to be scanned, in other words in accordance with the organ program which controls the X-ray device, e.g. for centered and decentered views. In another expansion stage, suitable means are provided for preferably automatic detection of the position and/or posture of the patient on the tabletop, e.g. suitable cameras in conjunction with suitable image analysis programs which detect the patient's relevant organ of interest for the next X-ray scan on the basis of the location and orientation of the patient and (automatically) move the X-ray generator to the desired scanning position relative to the organ in question via a link with the control means. This movement of the X-ray generator is then again tracked by the image receptor, so that in this case a particularly advantageous, preferably fully automatic sequence of operations for carrying out the X-ray scans is possible. Once the patient is positioned on the tabletop of the patient table, the X-ray generator is moved to the appropriate scanning position relative to the patient according to the organ program selected. The image receptor tracks the movement of the X-ray generator, namely the movement in the x- and y-direction and in accordance with the rotation of the collimator of the X-ray generator or the tilting movement of the X-ray generator so that, at the end of its movement, the image receptor is centered and is in the desired angular orientation below the X-ray generator. The desired X-ray scan of the patient is then carried out.

The invention can be used in particular in X-ray devices of simple and inexpensive design. However, ease of use such as that achieved by the automatic tracking of the image receptor does not have to be sacrificed.

The above described characteristics, features and advantages of this invention and the manner in which they are achieved will become clearer and more readily understandable in conjunction with the following description of the exemplary embodiments which will be explained with reference to the accompanying drawings, in which:

DESCRIPTION OF THE INVENTION

Figure 1:
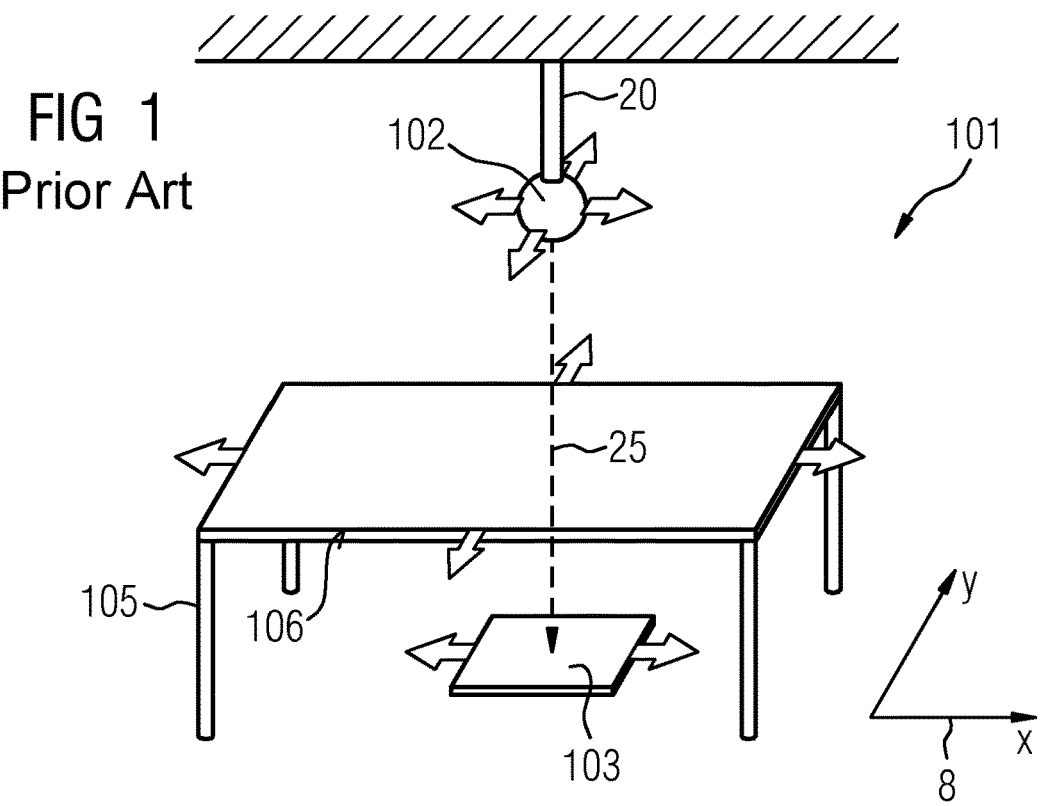
FIG. 1 shows a schematic representation of an X-ray generator, patient table and image receptor according to the prior art.

All the figures show the invention merely schematically and with its basic components. Identical reference characters correspond to elements having the same or comparable function.

An X-ray device 1 for a medical imaging system for radiological examination of patients 4 will now be described. In the example, this X-ray device 1 for radiographic examination (conventional X-ray) is disposed in an examination room.

According to the prior art, such an X-ray device 101 comprises an X-ray generator 102, an image receptor 103 which operates in conjunction with the X-ray generator 102 to carry out X-ray scans of the patient 4, and a patient table 105, the tabletop 106 of which is used to position the patient 4 during the X-ray scans, wherein the X-ray generator 102, which in the example is mounted on a ceiling-suspended stand 20, can be moved in the x- and y-direction, wherein the tabletop 106 can be moved in a floating manner in the x- and y-direction and wherein the image receptor 103, or more precisely the detector cabinet holding the image receptor 103, can be moved in the longitudinal direction of the table (x-direction) 8, see FIG. 1.

Figure 2:
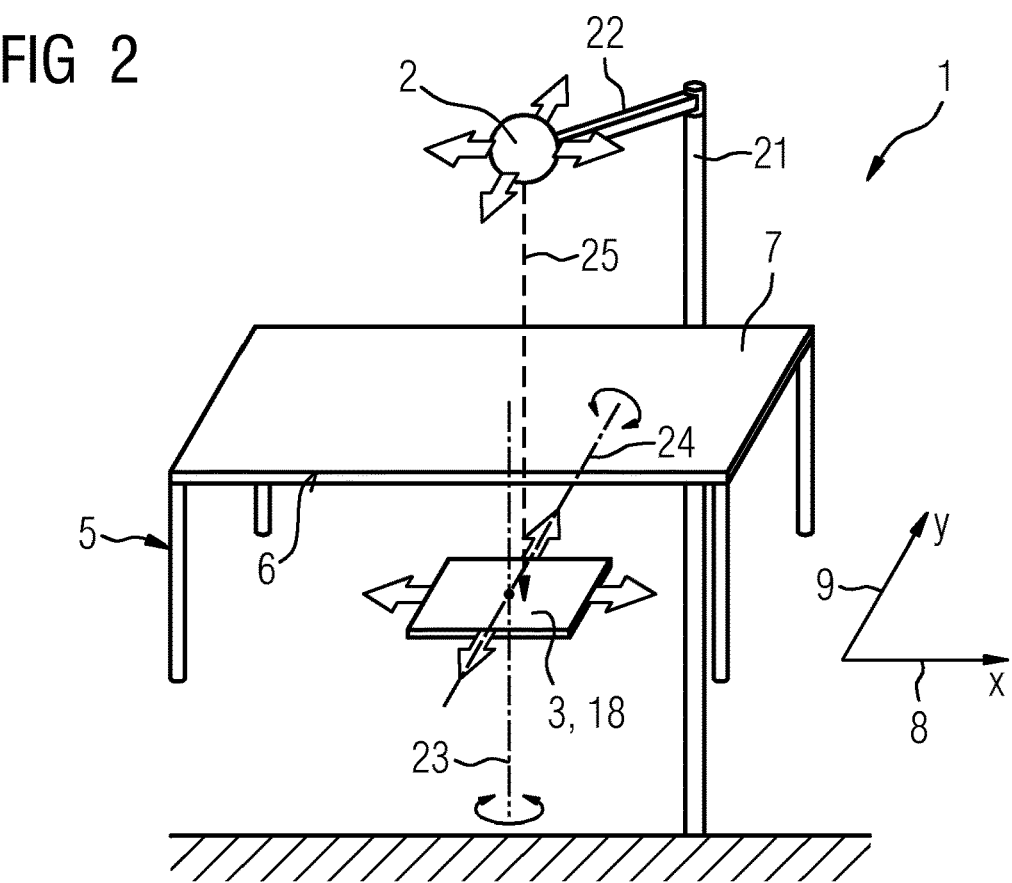
FIG. 2 shows a schematic view of an X-ray generator, patient table and image receptor according to the invention.
Figure 3:
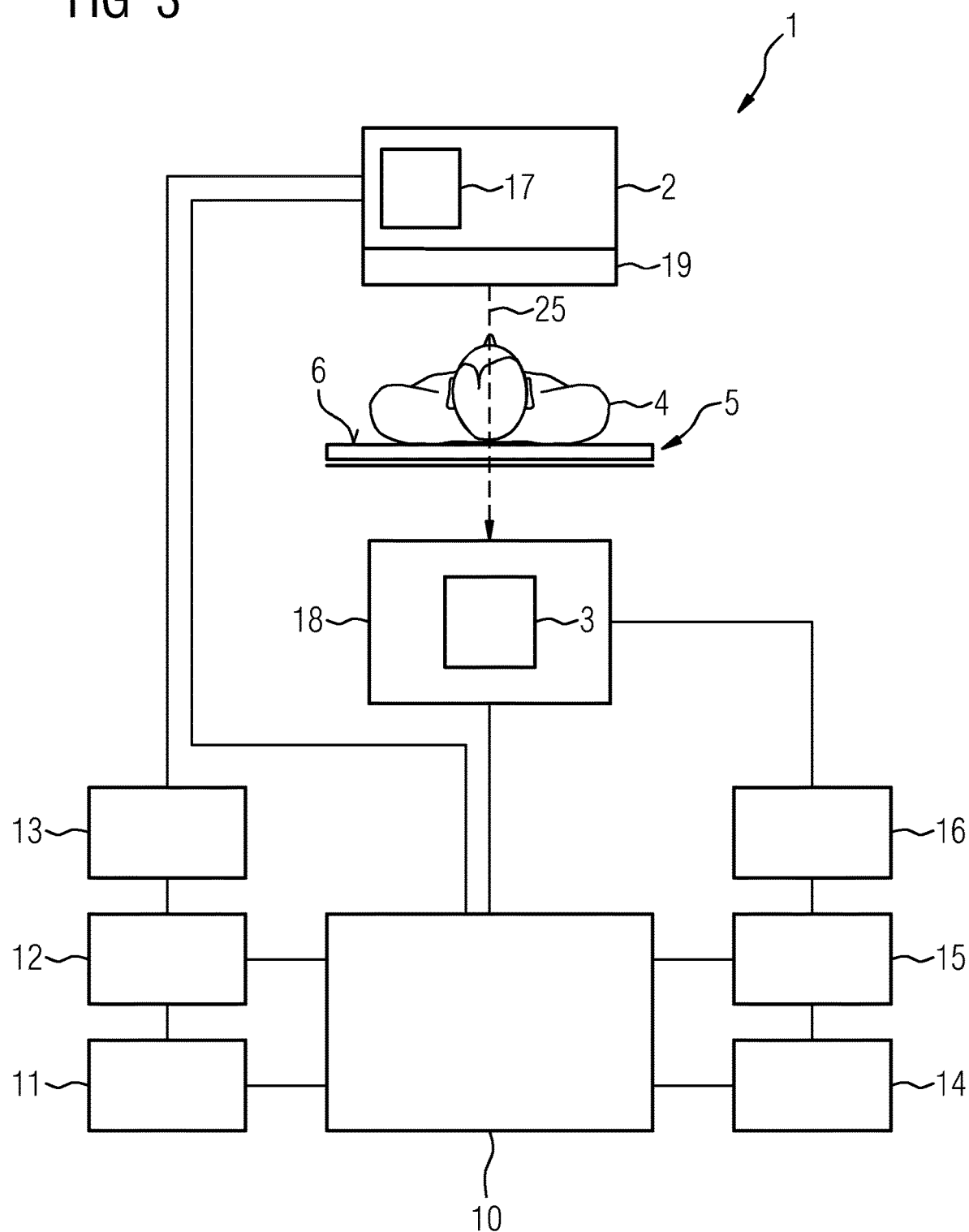
FIG. 3 shows a schematic view of the structural elements of the X-ray device according to the invention.

The X-ray device according to the invention 1, see FIG. 2 and FIG. 3, comprises an X-ray generator 2 likewise movable in the x- and y-direction, as well as a patient table 5 and an image receptor 3. The X-ray generator 2 is fixed to a floor stand 21.

The X-ray generator 2 comprises, as an X-ray source, an X-ray tube 17 enclosed by an X-ray protective housing. The high-voltage generator for operating the X-ray tube 17 is not shown. Attached to the X-ray protective housing is the collimator 19 with light-beam indicator. The collimator 19 consists of, among other things, lead leaf pairs for X-ray beam limiting, or more precisely for narrowing the beam of X-rays and reducing extrafocal radiation. The collimator 19 also comprises an X-ray-permeable mirror and a light source. This enables the X-ray field to be visually displayed on the patient 4.

The usually, as in the present example, horizontal position of the tabletop 6 defines the table plane 7 of the patient table 5. The tabletop 6 is fixed, i.e. immovable in the table plane (xy-plane) 7, i.e. both in the x-direction, i.e. in the table's longitudinal direction 8, and in the y-direction, i.e. in the table's transverse direction 9. However, this stationary tabletop 6 can be height-adjustable if the patient table 5 is a lifting table which can be raised or lowered in the direction of the floor or ceiling.

To carry out the X-ray scans, the position and/or posture of the patient 4 on the tabletop 6 is first automatically detected using suitable first position detection means 11 for detecting the position of the patient 4, e.g. a number of 3D cameras, and, depending on the detected position and/or posture and the selected organ program, the X-ray generator 2 is moved automatically by means of suitable first drive means 13, in particular using electric motor drives, to a desired scanning position, wherein said drive means 13 are controlled by first control means 12, e.g. a suitable motor controller.

According to the invention, a corresponding tracking movement takes place simultaneously with this orientation of the X-ray generator 2 or immediately thereafter, i.e. a corresponding positioning of the image receptor or more specifically an alignment of the image receptor with the X-ray generator 2. The X-ray detector 3 serving as an image receptor in the narrower sense in the example illustrated is enclosed in a detector cabinet 18 which is positioned under the tabletop 6. The detector cabinet 18 containing the X-ray detector 3 can be moved in the longitudinal direction of the table (x-direction) 8 and in the transverse direction (y-direction) 9 of the table relative to the tabletop 6 during the examination, i.e. between X-ray scans. Unlike the patient tables 105 known from the prior art, the patient tables 5 that can be used for the invention do not only have drive means 16 for moving the X-ray detector 3 or rather the detector cabinet 18 in the longitudinal direction of the table (x-direction) 8. In addition, these second drive means 16 are suitable for moving the X-ray detector 3 or rather the detector cabinet 18 in the transverse direction (y-direction) 9. The second drive means 16 are also designed to execute a rotational movement of the X-ray detector 3 or rather of the detector cabinet 18 and to execute a tilting movement of the X-ray detector 3 or rather of the detector cabinet 18. A combined swivel and tilt bearing (not shown) disposed under the tabletop allows a corresponding rotation of the X-ray detector 3 in the table plane 7, wherein the axis of rotation 23 is perpendicular to the xy-plane 7, and a corresponding tilting of the X-ray detector 3 in the table plane 7, wherein the tilt axis 24 is parallel with the xy-plane 7. The X-ray detector 3 is thus freely movable and positionable in the entire table plane 7 and can therefore assume the desired position relative to the X-ray generator 2. In particular, the X-ray detector 3 can be tilted in the case of oblique irradiation, so that the central ray 25 of the X-rays is also perpendicular to the image plane of the X-ray detector 3 in this case.

The second drive means 16 which are used to move the detector cabinet 18 (linear and rotational movement in the xy-plane 7 or tilting movement relative to the xy-plane 7) are electric motor drives. Said drives are controlled using second control means 15, such as suitable motor controllers. They are controlled such that the movement of the detector cabinet 18 and therefore the movement of the X-ray detector 3 takes place in accordance with the prior movement of the X-ray generator 2 and/or in accordance with the position assumed by the X-ray generator 2. These can be movements of the X-ray generator 2 in the x-direction 8 and/or y-direction 9 and/or rotational or tilting movements of the X-ray generator 2 or of parts of the X-ray generator 2. For this purpose the second control means 15 are connected to second position detection means 14, in particular suitable sensors, for detecting the position of the X-ray generator 2.

The inventive transverse movement of the X-ray detector 3 in the y-direction 9 must not be confused with movement of the X-ray detectors 3 at right angles to the longitudinal direction of the table which takes place during removal of the X-ray detector 3 from the detector cabinet 18. In other words, only transverse movements of the X-ray detector 3 relative to the detector cabinet 18 are known from the prior art, e.g. those involved in sliding the detector 3 into the detector cabinet 18 or out of the detector cabinet 18 on a plug-in tray (drawer principle). However, a transverse movement of the detector cabinet 18 holding the X-ray detector 3 is hitherto unknown. In other words, a common, linked movement of detector cabinet 18 and X-ray detector 3 in the y-direction 9 is as yet unknown. In this sense the term "image receptor" is always to be understood as meaning the combination of X-ray detector 3 and detector cabinet 18. Likewise little known hitherto is a transverse movement of the detector cabinet 18 as a tracking movement in accordance with a movement of the X-ray generator 2, namely dependent on a movement or position of the X-ray generator 2.

Instead of a "mobile" X-ray detector 3 that can be inserted in a detector cabinet 18, as described above, an image receptor that is "built-in" (in the sense of permanently connected to the patient table 5 or X-ray device 1) can be used with the present invention provided the inventive mobility of the image receptor is ensured.

The invention can be used with any type of X-ray device 1. However, it is particularly advantageous for it to be used with X-ray devices 1 whose X-ray generator 2 is mounted on a floor stand 21. X-ray devices 1 having such floor stands 21 are particularly inexpensive and therefore allow, in conjunction with the present invention, a design of the X-ray devices 1 with a particularly simple and robust construction which at the same time is reasonably priced.

In order that, in the case of a stationary patient table 5, the X-ray generator 2 can be moved to the desired scanning position above the corresponding organ of the patient 4 even when using a floor stand 21, the X-ray generator 2 is preferably mounted on a supporting arm 22 which can be pulled out or extended in some other suitable manner, particularly in order to allow the necessary longitudinal and transverse movement of the X-ray generator 2 relative to the patient table 5.

The method according to the invention can be carried out in a computer-assisted manner. It is particularly advantageous if at least the first or second position detection means 11, 14 and/or the first or second control means 12, 15 are implemented wholly or partially as a computer program. It is a known arrangement for the X-ray device 1 itself to have a central control unit 10 which is largely implemented as a computer program. The position detection means 11, 14 and control means 12, 15 are preferably implemented as parts of the central control unit 10 or connected thereto.

Although the invention has been illustrated and described in detail by the preferred exemplary embodiment, the invention is not limited to the examples disclosed and other variations will be apparent to persons skilled in the art without departing from the scope of protection sought for the invention.

The invention claimed is:

1. An X-ray device for a medical imaging system, the X-ray device comprising:
 an X-ray generator;
 an image receptor configured to operate in conjunction with said X-ray generator to carry out X-ray scans of a patient;
 a patient table having a tabletop for positioning the patient during the X-ray scans;
 said tabletop being immovably disposed in a table plane and said image receptor being mounted for movement in a plane parallel to said table plane in a longitudinal and transverse direction relative to said tabletop;
 said patient table including a motorized drive configured to move said image receptor based on a movement of said X-ray generator, such that movement of said image receptor tracks the movement of said X-ray generator based on a detected position of said X-ray generator; and
 said patient table additionally including at least one sensor configured to detect a position of the X-ray generator, and at least one controller configured to operate said motorized drive based on a signal from said at least one sensor.

2. The X-ray device according to claim 1, wherein said image receptor is rotatably mounted about an axis of rotation disposed perpendicular to the table plane and configured to tilt about a tilt axis parallel to said table plane.

3. The X-ray device according to claim 1, comprising a detector configured to detect a position and/or a posture of the patient on said tabletop and/or comprising a drive configured to move said X-ray generator to a scanning position.

4. The X-ray device according to claim 1, comprising a floor stand for supporting said X-ray generator.

5. The X-ray device according to claim 1, wherein said image receptor includes a detector cabinet positioned below said tabletop.

6. The X-ray device according to claim 1, wherein said image receptor is connected to the patient table.

7. A method for medical imaging, the method comprising the following steps:
positioning a patient on a tabletop of a patient table, the tabletop being immovable in a table plane;
moving an X-ray generator to a scanning position relative to the patient;
moving an image receptor that is longitudinally and transversely movable relative to the tabletop parallel to the table plane to a scanning position relative to the X-ray generator: based on a movement of said X-ray generator, such that movement of said image receptor tracks the movement of said X-ray generator based on a detected position of said X-ray generator;
the patient table including a drive for moving the image receptor, at least one sensor configured to detect a position of the X-ray generator, and at least one controller configured to operate the drive based on a signal from the at least one sensor; and
carrying out an X-ray scan of the patient.

8. A computer program for medical imaging by means of an X-ray device, comprising non-transitory computer program instructions for moving an X-ray generator to a scanning position relative to a patient who is positioned on a tabletop of a patient table, said tabletop being immovable in a table plane, for moving an image receptor that is disposed movably in a longitudinal and transverse direction relative to the tabletop parallel to the table plane to a scanning position relative to the X-ray generator, wherein the patient table has a drive for moving the image receptor and wherein the image receptor is moved based a movement of the X-ray generator, such that movement of the image receptor tracks the movement of said X-ray generator based on a detected position of said X-ray generator determined using a signal from at least one sensor configured to detect the position of said X-ray generator; and for carrying out an X-ray scan of the patient when the computer program instructions are executed in a control unit of the X-ray device.

* * * * *